United States Patent
Fomitchov

(10) Patent No.: US 7,144,370 B2
(45) Date of Patent: Dec. 5, 2006

(54) METHOD AND APPARATUS FOR IMAGING OF TISSUE USING MULTI-WAVELENGTH ULTRASONIC TAGGING OF LIGHT

(75) Inventor: Pavel Alexeyevich Fomitchov, New York, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/999,752

(22) Filed: Nov. 30, 2004

(65) Prior Publication Data

US 2005/0256403 A1    Nov. 17, 2005

Related U.S. Application Data

(60) Provisional application No. 60/570,645, filed on May 12, 2004.

(51) Int. Cl.
    *A61B 8/00*    (2006.01)
(52) U.S. Cl. ........................ 600/438; 600/473
(58) Field of Classification Search ............... 600/407, 600/425, 438, 473, 475, 477–480; 356/51, 356/303, 30
    See application file for complete search history.

(56) References Cited

U.S. PATENT DOCUMENTS

| | | | | |
|---|---|---|---|---|
| 4,479,499 A | * | 10/1984 | Alfano .................... | 600/477 |
| 5,127,405 A | * | 7/1992 | Alcala et al. .............. | 600/342 |
| 5,174,298 A | * | 12/1992 | Dolfi et al. ............... | 600/425 |
| 5,212,667 A | * | 5/1993 | Tomlinson et al. .......... | 367/7 |
| 5,309,912 A | * | 5/1994 | Knuttel ................... | 600/425 |
| 5,840,035 A | * | 11/1998 | Heusmann et al. .......... | 600/477 |
| 5,951,481 A | * | 9/1999 | Evans .................... | 600/473 |
| 6,002,958 A | * | 12/1999 | Godik ..................... | 600/407 |
| 6,041,248 A | * | 3/2000 | Wang .................... | 600/407 |
| 6,245,015 B1 | * | 6/2001 | Pattanayak ............... | 600/438 |
| 6,345,194 B1 | * | 2/2002 | Nelson et al. ............. | 600/425 |
| 6,466,806 B1 | * | 10/2002 | Geva et al. ............... | 600/310 |
| 6,738,653 B1 | * | 5/2004 | Sfez et al. ................ | 600/322 |
| 6,815,694 B1 | * | 11/2004 | Sfez et al. ............... | 250/492.1 |
| 6,957,096 B1 | * | 10/2005 | Sfez et al. ................ | 600/407 |
| 2004/0181143 A1 | * | 9/2004 | Israel .................... | 600/407 |
| 2005/0107694 A1 | * | 5/2005 | Jansen et al. ............. | 600/431 |

OTHER PUBLICATIONS

Balazs l. Bodai; Beth Boyd; Lurlene Brown; Harold Wadley; Victor J. Zannis; and Martin Holzman; Total Cost Comparison of 2 Biopsy Methods for Nonpalpable Breast Lesions; The American Journal of Managed Care, vol. 7, No. 5, May 2001; p.p. 527-538.

Tromberg BJ, Shah N, Lanning R, Cerussi A, Espinoza J, Pham T, Svaasand L, Butler J.; "Non-invasive in vivo characterization of breast tumors using photon migration spectroscopy"; Neoplasia. 2000 Jan.-Apr.; 2(1-2): 26-40.

(Continued)

*Primary Examiner*—Francis J. Jaworski
(74) *Attorney, Agent, or Firm*—Fletcher Yoder

(57) ABSTRACT

An imaging apparatus is disclosed. The imaging apparatus includes a source of electromagnetic radiation that is configured to emit electromagnetic radiation at two or more wavelengths through an imaging volume. The imaging apparatus also includes an ultrasound transducer that is configured to direct ultrasound waves through the imaging volume such that electromagnetic radiation passing through the imaging volume is modulated at the frequency of the ultrasound waves. The imaging apparatus further includes one or more electromagnetic radiation detectors that are configured to detect the modulated electromagnetic radiation from the imaging volume.

31 Claims, 2 Drawing Sheets

OTHER PUBLICATIONS

Figure 1:
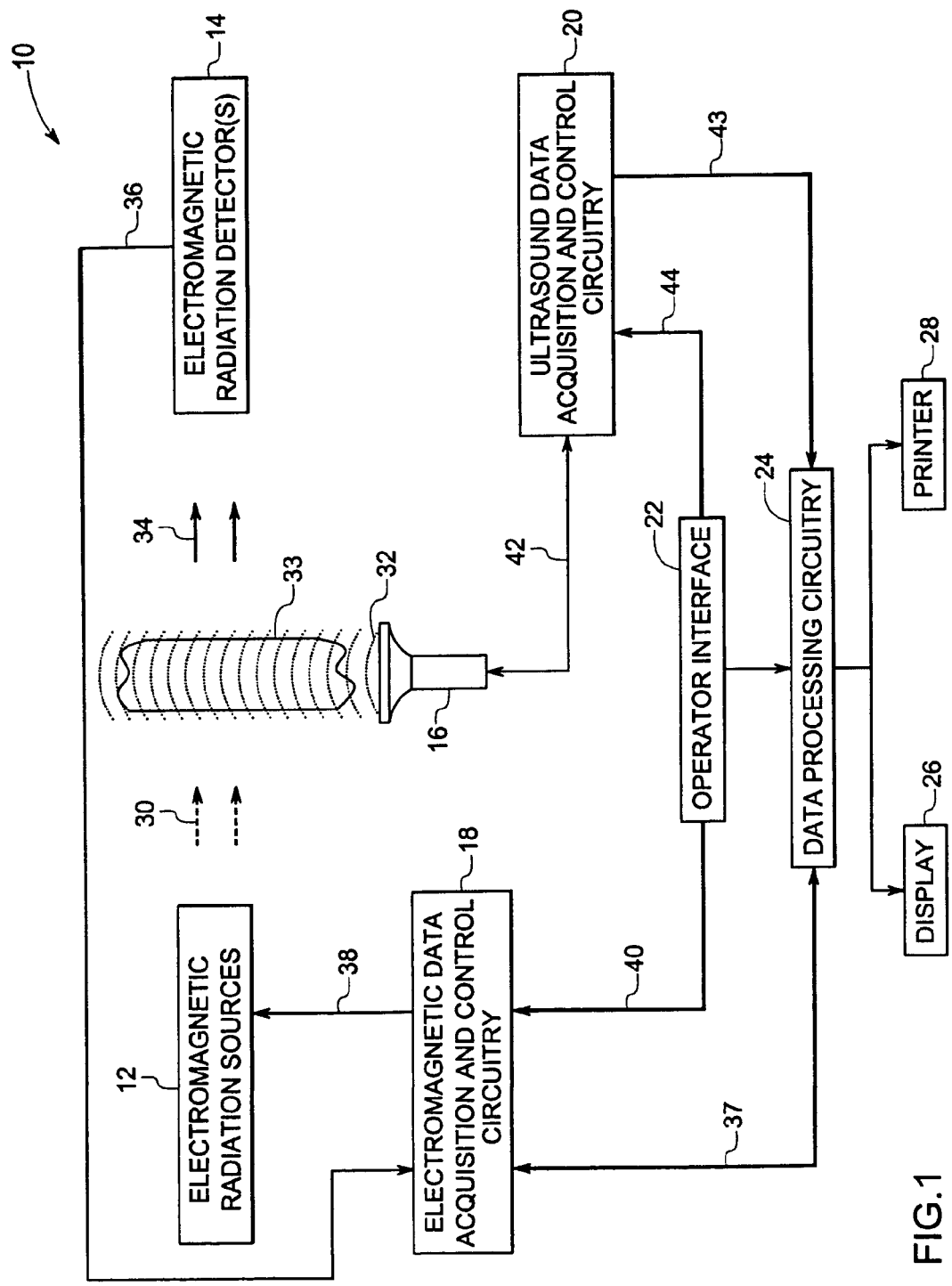

Vasilis Ntziachristos and Britton Chance; "Breast imaging technology: Probing physiology and molecular function using optical imaging—applications to breast cancer"; Breast Cancer Res. 2001; 3(1): 41-46.

Shah N, Cerussi A, Eker C, Espinoza J, Butler J, Fishkin J, Hornung R, Tromberg B.; "Noninvasive functional optical spectroscopy of human breast tissue"; Proc Natl Acad Sci U S A. 2001 Apr. 10; 98(8): 4420-4425.

Jun Li, Lihong V. Wang; "Methods for parallel-detection-based ultrasound-modulated optical tomography"; Applied Optics, vol. 41, Issue 10, Apr. 2002; 2079-2084.

McBride et al.; "Multispectral near-infrared tomography: a case study in compensating for water and lipid content in hemoglobin imaging of the breast"; Journal of Biomedical Optics /(1), 72-79 (Jan. 2002).

* cited by examiner

METHOD AND APPARATUS FOR IMAGING OF TISSUE USING MULTI-WAVELENGTH ULTRASONIC TAGGING OF LIGHT

CROSS REFERENCE TO RELATED APPLICATIONS

The present application claims priority to the provisional patent application No. 60/570,645, filed on May 12, 2004, and entitled "Method And Apparatus For Functional Imaging Of Biological Tissue Using Multi-Wavelength Ultrasonic Tagging Of Light".

BACKGROUND

The invention relates generally to the field of diagnostic medical imaging and more specifically, to non-invasive optical imaging.

In modern healthcare facilities, non-invasive imaging systems are often used for identifying, diagnosing, and treating physical conditions. Medical imaging typically encompasses the different non-invasive techniques to image and visualize the internal structures and/or functional behavior (such as chemical or metabolic activity) of organs and tissues within a patient. Currently, a number of modalities exist for medical diagnostic and imaging systems, each typically operating on different physical principles to generate different types of images and information. These modalities include ultrasound systems, computed tomography (CT) systems, x-ray systems (including both conventional and digital or digitized imaging systems), positron emission tomography (PET) systems, single photon emission computed tomography (SPECT) systems, and magnetic resonance (MR) imaging systems.

Another imaging modality is optical imaging, which operates by transmitting light of certain wavelengths through a patient and generating an image based on the transmitted light. Different wavelengths of light, including near infrared wavelengths, may be used for optical imaging. Due to light absorption and scattering by the imaged tissue, optical imaging typically has relatively poor spatial resolution and anatomical registration. For example, when optical imaging is employed for cancer detection, the imaging technique suffers from low or reduced sensitivity and specificity. It may, therefore, be desirable to improve the spatial resolution obtained in optical imaging.

BRIEF DESCRIPTION

In accordance with certain implementation of the present technique, an exemplary imaging apparatus is disclosed. The imaging apparatus includes a source of electromagnetic radiation that is configured to emit electromagnetic radiation at two or more wavelengths through an imaging volume. The imaging apparatus also includes an ultrasound transducer that is configured to direct ultrasound waves through the imaging volume such that electromagnetic radiation passing through the imaging volume is modulated at the frequency of the ultrasound waves. The imaging apparatus further includes one or more electromagnetic radiation detectors that are configured to detect the modulated electromagnetic radiation from the imaging volume.

In accordance with certain other implementation of the present technique, an exemplary method of imaging is disclosed. The method involves transmitting electromagnetic radiation at two or more wavelengths through a region of interest of an imaging volume and modulating the electromagnetic radiation in the region of interest using acoustic waves. The method further involves generating an image based on the modulated electromagnetic radiation.

DRAWINGS

Figure 2:
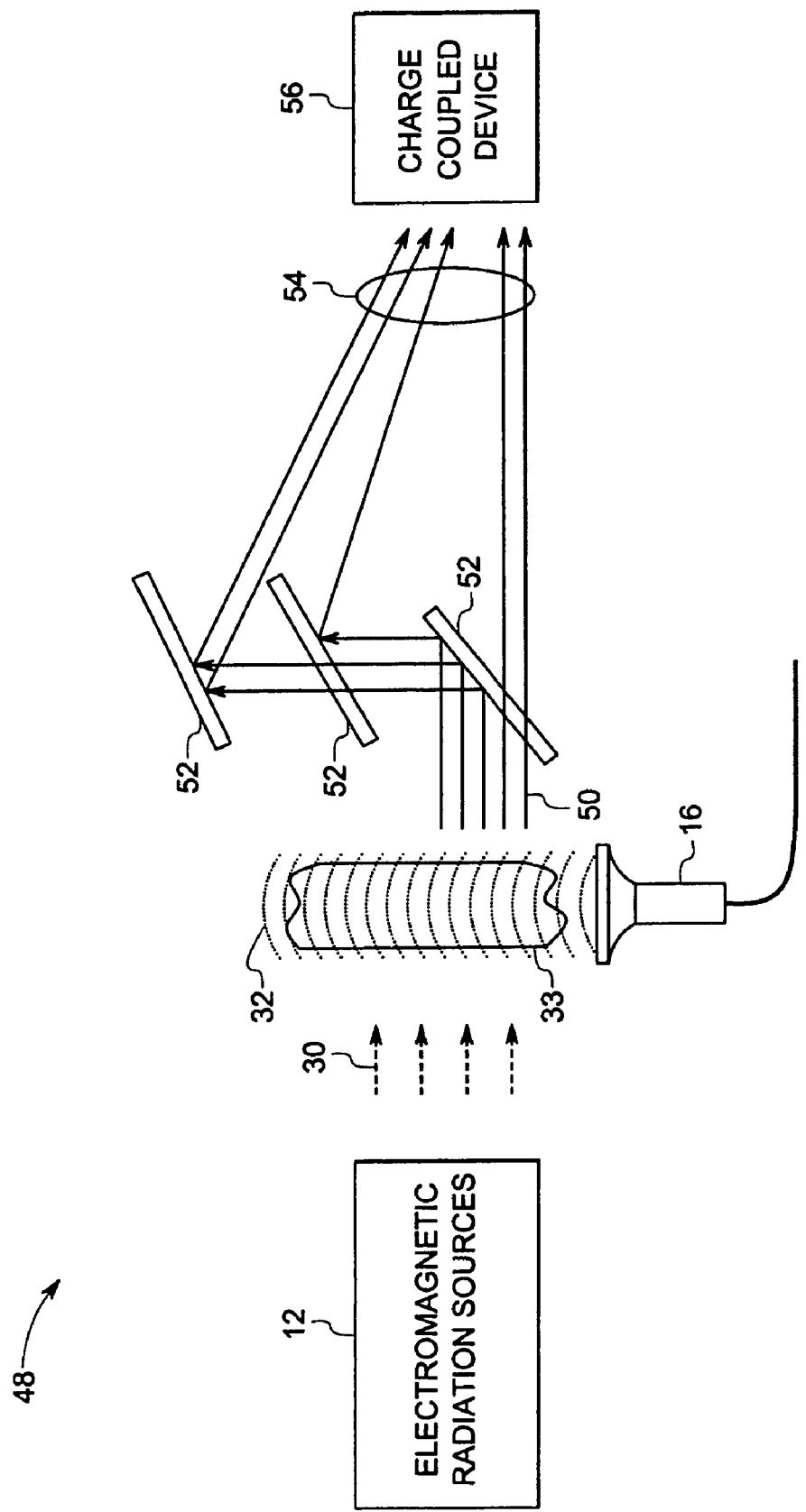

These and other features, aspects, and advantages of the present invention will become better understood when the following detailed description is read with reference to the accompanying drawings in which like characters represent like parts throughout the drawings, wherein:

FIG. 1 is a diagrammatical illustration of an exemplary imaging system for imaging biological tissues using multi-wavelength electromagnetic radiation and ultrasound; and FIG. 2 is a diagrammatical illustration of an exemplary embodiment of the imaging system using dichroic mirrors, optical filters and charge-coupled device in accordance with certain aspects of the present technique illustrated in FIG. 1.

DETAILED DESCRIPTION

Turning now to the drawings and referring first to FIG. 1, an exemplary imaging system 10 is illustrated. The depicted imaging system 10 includes a source 12 of electromagnetic radiation, a detector 14 of electromagnetic radiation, an ultrasound transducer 16, electromagnetic data acquisition and control circuitry 18, ultrasound data acquisition circuitry 20, operator interface 22, and data processing circuitry 24. The depicted exemplary imaging system 10 also includes a display 26 and a printer 28. The source 12 and detector 14 define an imaging volume which may accommodate part of a patient undergoing imaging, such as tissues 33 or organs being examined for signs of a disease or disorder.

The source 12 is configured to emit electromagnetic radiation 30 at two or more wavelengths. In one embodiment, the wavelengths are in a range from about 600 nanometers to about 900 nanometers, which is typically classified as near-infrared (NIR) radiation. As will be appreciated by those of ordinary skill in the art, the source 12 may encompass a common emission mechanism capable of emitting, concurrently or separately, the different wavelengths of light or separate emitters of the different wavelengths, such as discrete light emitting diodes (LEDs), laser diodes, or lasers. For example, in one embodiment, the source 12 may include one or more individual emitters of electromagnetic radiation, each emitter configured to emit at a specific wavelength. Examples of such emitters that may be incorporated into the source 12 include one or more lasers, laser diodes, light emitting diodes (LEDs), or their combinations. Typically, the coherence length of the emitted electromagnetic radiation is greater than the average path length difference due to scattering of the transmitted photons.

Furthermore, in certain exemplary implementations of the present technique, the two or more wavelengths of electromagnetic radiation may be emitted from the source 12 in a sequential or alternating manner, i.e., one after the other. In other exemplary implementations, the two or more wavelengths of electromagnetic radiation 30 may be emitted from the source 12 concurrently i.e., at the same time. The transmission of electromagnetic radiation 30 from the source 12 may occur in one of continuous wave mode, pulsed mode or intensity modulated mode.

The radiation emitted by the source 12 may be modulated by ultrasound waves propagating in the tissue 33. Ultrasound is acoustic energy in the form of waves having a frequency above the human hearing range, also called the sonic range. The highest frequency that the human ear can detect is about 20,000 Hertz. This is where the sonic range ends and the ultrasonic range begins. As will be appreciated by those of ordinary skill in the art, the ultrasound waves 32 may be generated by one or more devices, including piezo-electric transducers, capacitive micro-machined ultrasound transducers (cMUTs), ultrasound scanning phase arrays, and laser photo-acoustic generators.

The ultrasound transducer 16 emits ultrasound waves 32 that are directed at the tissue 33 or organ through which the electromagnetic radiation 30 is directed such that modulated electromagnetic radiation 34 emerges from the tissue 33. For example, in one embodiment, when electromagnetic radiation is focused on the tissue 33 or organ in a region of interest, and the ultrasound waves 32 are focused and scanned through the region of interest, the intensity or phase of the electromagnetic radiation passing through the tissue 33 or organ gets modulated at the frequency of the ultrasound waves. In other exemplary embodiments, the modulated electromagnetic radiation 34 is modulated at frequencies that are proportional to, but not substantially equivalent to, the frequency of the ultrasound waves. Due to the modulation, the modulated electromagnetic radiation 34 can be easily distinguished from background noise and/or from unmodulated electromagnetic radiation 30. As will be appreciated by a person skilled in the art, the ultrasound transducer 16 may operate in any of the operating modes known in the art. Examples of operating modes include continuous mode, toneburst mode, sweeped toneburst mode, or pulsed mode.

The detector 14 is adapted and configured to detect the modulated electromagnetic radiation 34. Since the intensity or phase electromagnetic radiation 34 is modulated based on the frequency of the ultrasound waves 32, the detector 14 may be configured to detect the modulated electromagnetic radiation 34, thereby allowing differential detection and processing of that electromagnetic radiation passing through the region of interest where the ultrasound is focused. Likewise, noise, such as unmodulated electromagnetic radiation, may be de-emphasized or ignored in subsequent processing, effectively providing a higher signal-to-noise ratio than might be attained without modulation.

In accordance with one embodiment of the present technique, the detector 14 includes one or more detector elements or mechanisms that are each configured to detect a specific wavelength of the modulated electromagnetic radiation 34. Conversely, in accordance with another embodiment, the detector 14 includes one or more detector elements or mechanisms, some or all of which are configured to detect multiple wavelengths of the modulated electromagnetic radiation 34. In this embodiment, separation of the modulated electromagnetic radiation 34 may be accomplished by sequential (as opposed to concurrent) emissions of the different wavelengths of electromagnetic radiation or by subsequent processing of the detected radiation. Examples of detectors include optical cameras, photomultiplier tubes (PMTs), photodiodes (including avalanche photodiodes), charge-coupled devices (CCDs), complementary metal oxide semiconductor (CMOS) devices, conventional full-field interferometers and photo-refractive devices. In certain implementations, the detector 14 may include a combination of one or more exemplary detectors specified above.

The electromagnetic data acquisition circuitry 18 acquires data 36 from the detector 14. In one embodiment, the circuitry 18 provides control signals 38 to the source 12 based on the data 36 to alter the wavelengths of the electromagnetic radiation 30 emitted by the source 12. In certain embodiments, the control signals 38 are based on the data 36 and on an imaging protocol or configuration 40 provided by an operator, such as via the operator interface 22. The control signals 38 control the operation of the source 12, such as by dynamically altering the spectral separation between the two or more wavelengths of electromagnetic radiation 30 to provide a high contrast between the required signal and background noise.

In one embodiment, the data acquisition circuitry 18 processes the data 36, such as digitizing, filtering, or otherwise preparing the data for subsequent communication and image processing. The acquired data 37 is provided to data processing circuitry 24, which generates an image 46 of the tissue or organ being imaged. The resulting image may be useful in determining differences in absorption coefficients of at the wavelengths emitted by the source 12. These differences may provide useful information, such as quantitative information about the different molecular states for biologically interesting molecules. For example, hypoxia may be an indicator of breast cancer which can be measured based upon the ratio of the concentrations of oxy- and deoxyhemoglobin. Because oxy and deoxyhemoglobin are differentially absorptive at different wavelengths, the present technique may be used to generate three-dimensional images quantifying the concentrations of oxy and deoxyhemoglobin in the imaged tissue, and thereby depicting local regions of hypoxia. The spatial resolution of the three-dimensional images is improved by the introduction of the ultrasound modulation of the electromagnetic radiation, which allows differential processing of that electromagnetic radiation transmitted through a region of interest in the tissue despite the scattering effects introduced by the tissue. In particular, the spatial resolution is determined by the size of the acoustic focal spot. The region of interest, typically, is the region that is visible to a system operator that identifies a region where imaging needs to be performed. Imaging volume, on the other hand, may be defined as the volume enclosed by the region of interest and containing the tissue 33 or organ that needs to be imaged and that which is not visible to the system operator. By scanning the ultrasound source 16 over the entire imaging volume of the tissue undergoing imaging, high resolution data be acquired for the entire region of interest and an image of the entire imaging volume may be generated which has improved spatial resolution. It should be noted that the purpose of modulation of the electromagnetic radiation by the ultrasound waves is to separate the electromagnetic radiation emanating from the imaged tissue from other electromagnetic radiation that may be emitted from other region or tissue not of specific interest.

In particular, in one embodiment, the spatial resolution of about 1 millimeter may be obtained by focusing ultrasound waves in the range of between 1 MHz to about 10 MHz. In this embodiment, the detector 14 is used to acquire a set of signals when coherent light (i.e., the electromagnetic radiation in this embodiment) is transmitted through tissue 33 alternating between compression and rarefaction states due to ultrasound waves 32. The data acquisition is performed in synchronization with generation of the ultrasonic wave in order to obtain signals corresponded to different phases of ultrasonic wave when it travels through the ultrasonic focus. By subtracting the signals in the rarefaction state from the signals obtained in the compression state, a full field ultrasonic modulated optical image is obtained. While subtracting the signals yields the full field ultrasound modulated optical image in this present embodiment, other techniques known in the art for extracting optical images from the signals may also be appropriately employed.

The preceding discussion dealt with the generation of three-dimensional functional images using ultrasound modulated electromagnetic radiation. In addition, as will be appreciated by those of ordinary skill in the arts, it may be desirable to generate an ultrasound image of the tissue in conjunction with the generated optical image. Such an exemplary combined modality imaging system providing images generated both on optical as well as ultrasound data would provide both structural and functional information to a reviewing technologist.

For example, referring now to the exemplary embodiment of FIG. 1, ultrasound data acquisition circuitry 20 is depicted which is configured to receive ultrasound data 42 from the ultrasound transducer 16. As will be appreciated by those of ordinary skill in the art, the ultrasound transducer 16 sends ultrasound waves 32 through the tissue 33 in the region of interest. Some of the ultrasound waves 32 are reflected back when they strike the tissue 33 and are detected by the ultrasound transducer 16. The operation of the transducer 16 controlled by the ultrasound data acquisition and control circuitry 20 by control instructions 44, which may in turn be based on an imaging protocol or configuration selected by an operator at the operator interface 22.

The ultrasound reflections and their respective timing information constitute ultrasound data 42, which is acquired by the ultrasound data acquisition and control circuitry 20. The ultrasound data 42 may be digitized and/or otherwise processed by the acquisition-circuitry 20. The acquired ultrasound data 43 is provided to data processing circuitry 24, which generates an image of the tissue or organ being imaged. In one embodiment, the acquired electromagnetic radiation data 36, typically optical data, and the acquired ultrasound data 43 are registered and processed to generate composite images for display on the display 26. In another embodiment, the acquired electromagnetic radiation data 36 and the acquired ultrasound data 43 are processed to generate separate images for display.

Turning now to FIG. 2, a specific detector embodiment is depicted as an example of one implementation in which the electromagnetic radiation 30 is concurrently emitted at different wavelengths. The exemplary imaging system 48 includes the source 12 (as illustrated in FIG. 1 and described previously) emitting electromagnetic radiation 30 in the form of coherent light at two or more wavelengths on a region of interest on the tissue 33. Ultrasound waves 32 from the ultrasonic transducer 16 are focused on the region of interest on the tissue 33 to modulate the coherent light, as described above. The modulated coherent light 50 that emerges from the region of interest is typically appears as a speckle pattern, where the speckle patterns are field intensity patterns produced by mutual interference of coherent light when subjected to minute spatial and temporal fluctuations during propagation through a scattering medium. This modulated coherent light 50 is separated into individual wavelengths by a dichroic mirror assembly having a set of dichroic mirrors (designated by reference numeral 52). The set of two or more dichroic mirrors are designed to reflect certain wavelengths of light and allow the passage of other wavelengths of light. The separated wavelengths of modulated coherent light 50 are then detected by a CCD device 56, such as a full field gated CCD camera, in the depicted embodiment. The separated individual wavelengths of the modulated coherent light 50 are then focused on a CCD device 56 via an objective 54. This optical arrangement images the separated speckle patterns onto different areas of the CCD device. This allows for simultaneous registration of multiple speckle patterns formed by separated wavelengths.

In certain other exemplary implementations of the present technique, one or more optical band pass filters may be used to separate the two or more wavelengths of the modulated coherent light.

As will be appreciated by those of ordinary skill in the art, other implementations of the detector 14 may be employed to detect ultrasound-induced modulation of electromagnetic radiation in which two or more wavelengths of radiation are present. For example, photorefractive interferometers or conventional speckle interferometers in combination with band pass filters and dichroic mirrors may be used to detect ultrasonic-induced modulation. Likewise, multiple CCD devices 56 may be employed such that different wavelengths of modulated radiation are detected on different CCD devices 56. Furthermore, a fiber bundle based splitter, with or without band pass optical filters, may constitute part of the detector 14.

In accordance with certain implementations of the present technique, an exemplary method of diagnosing a disorder in a tissue or organ includes the step of detecting the modulated electromagnetic radiation at a first wavelength and a second wavelength transmitted through the tissue. As explained previously, modulation of the electromagnetic radiation is achieved by focusing ultrasound waves on the region of interest containing the tissue. The electromagnetic radiation incident and passing through the tissue gets modulated at the ultrasound frequency. Moreover, it must be particularly noted that detection of the modulated electromagnetic radiation may be achieved by any of the devices specified and described earlier. The method further involves calculating a difference in absorption of each wavelength of the modulated electromagnetic radiation at different locations in the tissue. The method may involve diagnosing any disorder based on the difference in absorption of electromagnetic radiation at the first and the second wavelength. In certain other implementations, electromagnetic radiation at two or more wavelengths may also be used. An image of the tissue may further be generated based on the detected modulated electromagnetic radiation.

In accordance with certain other exemplary implementations of the present technique, a method of using an imaging system includes the step of operating an optical imaging subsystem configured to emit electromagnetic radiation at two or more wavelengths through an imaging volume. The method further involves operating an ultrasound transducer configured to direct ultrasound waves through the imaging volume such that electromagnetic radiation passing through the imaging volume is modulated based on the frequency of the ultrasound waves. It must be particularly noted that an imaging system while operating under principles of the present technique provides an improved spatial resolution.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging apparatus, comprising:
   a source of electromagnetic radiation configured to emit electromagnetic radiation at two or more wavelengths through an imaging volume;
   an ultrasound transducer configured to direct ultrasound waves through the imaging volume such that electromagnetic radiation passing through the imaging volume is modulated based on the frequency of the ultrasound waves; and one or more electromagnetic radiation detectors configured to detect the electromagnetic radiation; wherein each wavelength is detected at a separate portion of the one or more detectors.

2. The imaging apparatus as recited in claim 1, wherein the two or more wavelengths are within a near-infrared spectrum.

3. The imaging apparatus as recited in claim 1, wherein the source of electromagnetic radiation comprises at least one coherent electromagnetic radiation source for each wavelength.

4. The imaging apparatus as recited in claim 1, wherein the source of electromagnetic radiation comprises at least one light emitting diode, laser diode or laser for each wavelength.

5. The imaging apparatus as recited in claim 1, wherein electromagnetic radiation is transmitted in one of a continuous wave mode, a pulsed wave mode or an intensity modulated wave mode.

6. The imaging apparatus as recited in claim 1, further comprising electromagnetic data acquisition and control circuitry configured to receive data from the one or more electromagnetic radiation detectors.

7. The imaging apparatus as recited in claim 1, further comprising ultrasound data acquisition and control circuitry configured to acquire ultrasound data via the ultrasound transducer.

8. The imaging apparatus as recited in claim 1, comprising data processing circuitry configured to generate an image based on data acquired by at least one of the one or more electromagnetic radiation detectors or the ultrasound transducer.

9. The imaging apparatus as recited in claim 1, wherein the two or more wavelengths are within a range of about 600 nanometers to about 900 nanometers.

10. The imaging apparatus as recited in claim 1, wherein the one or more electromagnetic radiation detectors comprise at least one of a charge-coupled device, a complementary metal oxide semiconductor device, a photomultiplier tube device, a photo-refractive interferometer, a full field speckle interferometer, or combinations thereof.

11. The imaging apparatus as recited in claim 1, comprising a dichroic mirror assembly configured to separate the two or more wavelengths of electromagnetic radiation such that each wavelength is detected at the respective separate portion of the one or more detectors.

12. The imaging apparatus as recited in claim 1, wherein the one or more electromagnetic radiation detectors comprise one or more band pass optical filters configured to separate the electromagnetic radiation into the two or more wavelengths such that each wavelength is detected at the respective separate portion of the one or more detectors.

13. The imaging apparatus as recited in claim 1, wherein the ultrasound transducer comprises one of a piezoelectric ultrasound transducer, a capacitive ultrasound transducer, an ultrasonic scanning phase array, a laser photo-acoustic generator, or combinations thereof.

14. The imaging apparatus as recited in claim 1, wherein the source of electromagnetic radiation operates in a continuous wave mode, an intensity modulated mode, or a pulsed mode.

15. A method of imaging, comprising:
 transmitting electromagnetic radiation at two or more wavelengths through a region of interest;
 modulating the electromagnetic radiation in the region of interest using acoustic waves; and
 detecting each wavelength of the electromagnetic radiation on a respective separate portion of one or more electromagnetic radiation detectors.

16. The method as recited in claim 15, comprising generating the acoustic waves via an ultrasound transducer.

17. The method of claim 15 comprising generating an image using the detected electromagnetic radiation.

18. The method of claim 15 comprises generating an image using the detected electromagnetic radiation and the acoustic waves.

19. The method as recited in claim 15, wherein frequency of the modulated radiation is linearly proportional to frequency of the acoustic waves.

20. The method as recited in claim 15, comprising separating the electromagnetic radiation into the two or more wavelengths using one or more band pass filters.

21. The method as recited in claim 15, comprising separating the two or more wavelengths of electromagnetic radiation using a dichroic mirror assembly.

22. The method as recited in claim 15, comprising separating the two or more wavelengths of electromagnetic radiation using one or more prisms.

23. The method as recited in claim 15, further comprising dynamically altering the frequency of the acoustic waves.

24. The method as recited in claim 15, further comprising dynamically altering the two or more wavelengths of electromagnetic radiation.

25. A method of diagnosing a disorder, comprising:
 detecting electromagnetic radiation at two or more substantially discrete wavelengths concurrently transmitted through a tissue, wherein the electromagnetic radiation is acoustically modulated by an external source directed at the tissue; and
 calculating a difference in absorption of each wavelength of the modulated electromagnetic radiation at different locations in the tissue.

26. The method of claim 25, comprising diagnosing a disorder based on the differences in absorption.

27. The method of claim 25, comprising generating an image conveying the differences in absorption within the tissue.

28. The method as recited in claim 25, comprising modulating the electromagnetic radiation by directing ultrasound waves at the tissue while transmitting electromagnetic radiation at the two or more wavelengths through the tissue.

29. The method as recited in claim 28, comprising generating an image based on the ultrasound waves.

30. The method as recited in claim 28, comprising generating an image based on the ultrasound waves and the modulated electromagnetic radiation.

31. A method of using an imaging system, comprising:
 operating an optical imaging subsystem configured to concurrently emit electromagnetic radiation at two or more substantially discrete wavelengths through an imaging volume; and
 operating an ultrasound transducer configured to direct ultrasound waves through the imaging volume such that electromagnetic radiation passing through the imaging volume is modulated based on the frequency of the ultrasound waves.

* * * * *